United States Patent [19]

Miki et al.

[11] Patent Number: 4,956,183

[45] Date of Patent: Sep. 11, 1990

[54] COMPOSITION COMPRISING COPPER COMPOUND

[75] Inventors: Yoshiaki Miki, Yokohama; Tsunehisa Ueda, Zushi, both of Japan

[73] Assignee: Nippon Zeon Co., Ltd., Tokyo, Japan

[21] Appl. No.: 82,346

[22] Filed: Aug. 6, 1987

[30] Foreign Application Priority Data

Aug. 7, 1986 [JP] Japan .................. 61-186066

[51] Int. Cl.$^5$ ............................................. A21N 59/20
[52] U.S. Cl. .................... 424/630; 424/637; 514/185; 514/499
[58] Field of Search ............... 514/499, 185; 424/125, 424/123, 145, 140, 141, 143, 145, 630, 637

[56] References Cited

U.S. PATENT DOCUMENTS

| | | | |
|---|---|---|---|
| 2,856,330 | 10/1988 | Vagenius | 424/84 |
| 3,124,459 | 3/1964 | Erwin | 99/1 |
| 3,124,460 | 3/1964 | Erwin | 99/1 |
| 3,172,817 | 3/1965 | Leupold | 424/90 |
| 4,447,243 | 5/1984 | Claiborne | 424/76 |
| 4,511,552 | 4/1988 | Cox | 424/76 |
| 4,622,248 | 11/1986 | Leach et al. | 514/499 |
| 4,719,105 | 1/1988 | Schleppnik | 424/76.21 |

FOREIGN PATENT DOCUMENTS

| | | | |
|---|---|---|---|
| 967515 | 8/1964 | United Kingdom | 514/499 |
| 1424345 | 2/1976 | United Kingdom | 514/499 |

OTHER PUBLICATIONS

Avakyan et al., Chem. Abst. 75(4): 31794q (1971).
Lange, N. A., *Handbook of Chemistry*, 10th Ed. (1967), pp. 830–832.

*Primary Examiner*—Leonard Schenkman
*Attorney, Agent, or Firm*—Sherman and Shalloway

[57] ABSTRACT

A composition comprising a copper compound, and blended with it, an oxocarboxylic acid compound. The composition has excellent deodorizing, fungicidal and moldproof properties.

13 Claims, No Drawings

COMPOSITION COMPRISING COPPER COMPOUND

This invention relates to a novel composition comprising a copper compound. More specifically, it relates to a novel composition having excellent deodorizing, fungicidal and moldproof properties comprising a copper compound, and blended with it, an oxocarboxylic acid compound and as required, water.

Copper sulfate, copper chloride and other various copper compounds are utilized as raw materials in a variety of applications, for example for the production of deodorants, fungicides, insecticides, agricultural chemicals, pharmaceuticals and catalysts. In particular, they are known to have excellent deodorizing and fungicidal properties. Generally, however, many of them are toxic and cannot be used in large amounts. Hence, these copper compounds have the defect of finding only limited utility from the standpoint of safety and performance.

The present inventors have made extensive investigations in order to improve such properties of copper compounds and permit their use in lesser amounts, and have consequently found that the incorporation of an oxocarboxylic acid compound in the copper compound is effective. This finding has led to the present invention.

Thus, according to this invention, there is provided a novel composition comprising a copper compound, an oxocarboxylic acid compound and, as required, water.

The copper compound used in this invention may be any of those compounds which contain copper, for example, inorganic acid salts, organic acid salts, complexes, hydroxides, sulfides and oxides of copper. Specific examples include copper sulfate, copper nitrate, cuprous chloride, cupric chloride, cuprous bromide, cupric bromide, cuprous iodide, copper carbonate, cupric hydroxide, cupric sulfide, copper cyanide, copper acetate, cupric citrate, copper glyoxylate, copper 2-ketoglutarate, copper pyruvate, copper oxalacetate, copper pyrophosphate, copper chlorophyll, copper chlorophyllin sodium, copper phthalocyanine, copper porphyrin, cuprous oxide and cupric oxide. Among them, the inorganic acid salts are preferred from the viewpoint of cost and availability, and the complexes are preferred because of safety.

It should be understood that when the copper compound is a copper oxocarboxylate, the composition of this invention contains the copper compound and the oxocarboxylic acid compound without separately adding the oxocarboxylic acid compound.

The oxocarboxylic acid compound used in this invention is an oxocarboxylic acid compound having from 2 to 8 carbon atoms and containing at least one aldehyde or keto group and at one carboxyl group in the molecule, or its water-soluble salt. Specific examples include glyoxylic acid, malonaldehyde acid, succinaldehyde acid, pyruvic acid, 2-ketobutyric acid, 4-acetylbutyric acid, 2-ketoglutaric acid, 4-keto-n-valeric acid, acetoacetic acid, oxomalonic acid, oxaloacetic acid, and acetonedicarboxylic acid, and sodium, potassium and ammonium salts of these compounds.

The amount of the oxocarboxylic acid compound blended may be properly chosen according to the properties required of the final composition of this invention. Usually, it is 0.1 to 1000 moles, preferably 0.2 to 100 moles, per mole of the copper ion in the copper compound.

As required, the composition of this invention may be used in combination with conventional deodorants, fungicides and moldproof agents, or various additives such as pigments, coloring agents, stabilizers and antioxidants may be added to the composition, so long as these additional agents do not impair the functions of the composition of this invention.

There is no particular restriction on the method by which the composition of this invention is prepared. For example, the individual components are uniformly dissolved in water to form the composition as an aqueous solution. The aqueous solution may be dried by, for example, lyophilization or spray drying to obtain the composition as a dry mixture. Alternatively, crystalline powders of the individual components may be uniformly mixed to obtain the composition as a dry mixture.

The form of the composition is neither restricted in particular. It may, for example, be in the form of an aqueous solution, or a solid composition (such as a powder or a tablet). As required, the aqueous solution may be impregnated or coated in or on an impregnatable or coatable substrate such as paper, cloths, foamed sheets, pulp, and fibers. It may also be supported on a carrier such as bentonite, activated carbon and zeolite. The amount of the composition based on the substrate or carrier is not particularly restricted, and may vary according to the use to which it is put and the method of using it. Usually, it is 10 to 20% by weight as solids. If the amount of the composition is excessively small, its function might be insufficient. Excessively large amounts are sometimes uneconomical.

Thus, the present invention can give a novel composition which has improved functions such as improved deodorizing ability over the copper compound alone and permits decrease of the amount of the copper compound used. This composition is useful as a raw material for a deodorant, a fungicide, a moldproof agent, etc.

The following Examples and Comparative Examples illustrate the present invention more specifically. In all these examples, parts and percentages are by weight unless otherwise specified.

In each run, predetermined amounts of each of the copper compounds and each of the oxocarboxylic acids indicated in Table 1 were dissolved in distilled water to prepare a 10% aqueous solution.

Thirty milligrams of the resulting aqueous solution was put in a 100 ml Erlenmeyer flask, and the flask was stopped. One milliliter of ethylmercaptan (0.5 g/3 liter $N_2$) was added. Ethylmercaptan in the vapor phase was periodically quantified by gas chromatography, and the ratio of decrease of ethylmercaptan (as a measure of mercaptan deodorizing ability) was calculated. The results are shown in Table 1.

Separately, 100 mg of the aqueous solution was put in a 100 ml Erlenmeyer flask, and the flask was stopped. Then, 50 microliters of a 28% aqueous solution of ammonia was added, and ammonia in the vapor phase was periodically quantified by gas chromatography, and the ratio of decrease of ammonia (a measure of ammonia deodorizing ability) was calculated. The results are also shown in Table 1.

TABLE 1

| Run No. | Copper compound (parts) | | | Oxocarboxylic acid (parts) | | Mole ratio (*1) | Decrease ratio (%) of ethylmercaptan | | | Decrease ratio of ammonia | | |
|---|---|---|---|---|---|---|---|---|---|---|---|---|
| | Copper sulfate pentahydrate | Cupric chloride | Copper chlorophyllin sodium | 2-ketoglutaric acid | Glyoxylic acid | | 5 min. later | 10 min. later | 30 min. later | 1 min. later | 5 min. later | 10 min. later |
| Example | | | | | | | | | | | | |
| 1-1 | 90 | — | — | 10 | — | 0.2 | 69 | 95 | 100 | 90 | 96 | 100 |
| 1-2 | 70 | — | — | 30 | — | 0.7 | 78 | 100 | — | 91 | 96 | 100 |
| 1-3 | 30 | — | — | 70 | — | 4 | 69 | 94 | 100 | 86 | 94 | 100 |
| 1-4 | 10 | — | — | 90 | — | 15 | 58 | 76 | 100 | 91 | 93 | 99 |
| 1-5 | 1 | — | — | 99 | — | 170 | 12 | 22 | 40 | 90 | 92 | 100 |
| 1-6 | 70 | — | — | — | 30 | 1.2 | 83 | 100 | — | 89 | 95 | 100 |
| 1-7 | — | 70 | — | 30 | — | 0.4 | 87 | 100 | — | 83 | 87 | 97 |
| 1-8 | — | — | 70 | 30 | — | 1.9 | 40 | 61 | 82 | 71 | 88 | 98 |
| Comparative Example | | | | | | | | | | | | |
| 2-1 | 100 | — | — | — | — | — | 66 | 93 | 100 | 82 | 98 | 100 |
| 2-2 | 1 | — | — | — | — | — | 3 | 4 | 15 | 13 | 24 | 31 |
| 2-3 | — | 100 | — | — | — | — | 89 | 98 | 100 | 77 | 92 | 100 |
| 2-4 | — | — | 100 | — | — | — | 25 | 36 | 79 | 2 | 7 | 8 |
| 2-5 | — | — | — | 100 | — | — | 0 | 0 | 0 | 92 | 96 | 99 |
| 2-6 | — | — | — | — | 100 | — | 0 | 0 | 0 | 79 | 83 | 96 |

(*1): Moles of the oxocarboxylic acid per mole of the copper ion in the copper compound.

Table 1 shows that even when the amount of the copper compound in the composition of this invention is decreased to about 10 %, the mercaptan deodorizing ability of the composition is maintained owing to the synergistic effect of the copper compound and the oxocarboxylic acid without impairing its ammonium deodorizing ability; that even when the amount of the copper compound is extremely decreased (Run No. 1-5), the composition exhibits much better performance than in the case of using the copper compound alone (Run No. 2-2); and that the compositions show similar excellent deodorizing performance even when the types of the copper compound and the oxocarboxylic acid were changed (Runs Nos. 1-6 to 1-8).

What is claimed is:

1. A deodorant composition comprising a mixture of a copper compound selected from the group consisting of inorganic acid salts of copper and complexes of copper, and oxocarboxylic acid compound having from 2 to 8 carbon atoms and at least one aldehyde or keto group and at least one carboxyl group in the molecule, the amount of oxocarboxylic acid compound in said mixture being from 0.2 to 100 moles, per mole of the copper ion in the copper compound.

2. The deodorant composition of claim 1 wherein the copper compound is copper sulfate, cupric chloride or copper chlorophyllin sodium.

3. The deodorant composition of claim 1 wherein the oxocarboxylic acid is 2-ketoglutaric acid or glyoxylic acid.

4. The deodorant composition of claim 1 wherein the copper compound is copper sulfate or cupric chloride.

5. The deodorant composition of claim 1 wherein the copper compound is copper chlorophyllin sodium.

6. A solid deodorizing composition comprising a mixture of a copper compound selected from the group consisting of 2-ketoglutaric acid and glyoxylic acid. chlorophyllin sodium, and from 0.2 to 100 moles, per mole of the copper ion in the copper compound, of an oxocarboxylic acid compound selected from the group consisting of 2-ketoglutaric acid and glyoxylic acid.

7. The solid deodorizing composition of claim 6 wherein the copper compound is copper sulfate or cupric chloride.

8. The solid deodorizing composition of claim 6 wherein the copper compound is copper chlorophyllin sodium.

9. An aqueous composition exhibiting mercaptan deodorizing ability and ammonium deodorizing ability and comprising an aqueous solution of a copper compound selected from the group consisting of copper sulfate, cupric chloride and copper chlorophyllin sodium and an oxocarboxylic acid selected from the group consisting of 2-ketoglutaric acid and glyoxylic acid, the amount of the oxocarboxylic acid being from 0.2 to 100 moles, per mole of the copper ion in the copper compound.

10. The deodorizing composition of claim 9 wherein the copper compound and oxocarboxylic acid are mixed at a ratio in the range of from 90:10 to 1:99.

11. The deodorizing composition of claim 9 wherein the amounts of the copper compound and oxocarboxylic acid compound provide a ten percent aqueous solution.

12. The deodorizing composition of claim 9 wherein the copper compound is copper sulfate or cupric chloride.

13. The deodorizing composition of claim 9 wherein the copper compound is copper chlorophyllin sodium.

* * * * *

UNITED STATES PATENT AND TRADEMARK OFFICE
CERTIFICATE OF CORRECTION

PATENT NO. : 4,956,183
DATED : September 11, 1990
INVENTOR(S) : MIKI, ET AL.

It is certified that error appears in the above-identified patent and that said Letters Patent is hereby corrected as shown below:

Column 4, Line 24;

Claim 6, line 3, delete "2-ketoglutaric acid and glyoxylic acid.", insert --copper sulfate, cupric chloride and copper--.

Signed and Sealed this

Seventh Day of July, 1992

Attest:

DOUGLAS B. COMER

Attesting Officer      Acting Commissioner of Patents and Trademarks